United States Patent
Chang

(10) Patent No.: US 8,322,302 B2
(45) Date of Patent: *Dec. 4, 2012

(54) **METHOD FOR BREEDING *MUSCA DOMESTICA***

(75) Inventor: Chun-Hsung Chang, Chang-Hua Hsien (TW)

(73) Assignee: New I Ten Rin Enterprise Co., Ltd., Chang-Hua Hsien (TW)

( * ) Notice: Subject to any disclaimer, the term of this patent is extended or adjusted under 35 U.S.C. 154(b) by 206 days.

This patent is subject to a terminal disclaimer.

(21) Appl. No.: 12/955,979

(22) Filed: Nov. 30, 2010

(65) Prior Publication Data

US 2012/0132140 A1    May 31, 2012

(51) Int. Cl.
*A01K 29/00* (2006.01)
(52) U.S. Cl. .......................... 119/6.5; 119/6.6
(58) Field of Classification Search .............. 119/6.5, 119/6.6; 424/76.5, 76.6
See application file for complete search history.

(56) References Cited

U.S. PATENT DOCUMENTS

| | | | |
|---|---|---|---|
| 4,594,964 A * | 6/1986 | Vargas et al. | 119/6.6 |
| 6,557,487 B1 * | 5/2003 | Fleischmann | 119/6.5 |
| 6,938,574 B2 * | 9/2005 | Zhang | 119/6.6 |
| 2002/0177219 A1 * | 11/2002 | Olivier | 435/262 |
| 2003/0143728 A1 * | 7/2003 | Olivier | 435/290.1 |
| 2003/0233982 A1 * | 12/2003 | Zhang | 119/6.5 |
| 2004/0089241 A1 * | 5/2004 | Zhang | 119/6.5 |
| 2011/0296756 A1 * | 12/2011 | Zhang | 47/59 R |

OTHER PUBLICATIONS

Larry Newton Using the Black Soldier Fly, *Hermetia illucens*, Value added tool for the Management of swine manure, North Carolina State University (USA) Jun. 2006.*

Joseph Diclaro and Phillip Kaufman 'Black soldier fly *Hermetia illucens* Linnaeus (insecta: Diptera: Stratiomyidae)' EENY-461, IFAS Extension, University of Florida (USA), Jun. 2009.*

* cited by examiner

*Primary Examiner* — Isam Alsomiri
*Assistant Examiner* — Justin Benedik
(74) *Attorney, Agent, or Firm* — Alan Kamrath; Kamrath IP Lawfirm, PA

(57) ABSTRACT

A method for breeding *Musca Domestica* includes placing imagoes of *Musca Domestica* in an environment having a temperature of 18-35° C. and having a humidity of 50-80%. A laying pan is provided to attract the imagoes of *Musca Domestica* to lay eggs in the laying pan. The laying pan includes substances capable of attracting the imagoes of *Musca Domestica* to lay eggs in the laying pan. The eggs are transferred into a cultivating material including at least one product of soybean and/or milk. The eggs of *Musca Domestica* are bred at a temperature of 20-35° C. until hatching into larvae. The larvae are placed on swine feces and bred at a temperature of 20-35° C. for 2-3 days. The yield and breeding speed of the larvae of *Musca Domestica* are increased by the method.

14 Claims, 1 Drawing Sheet

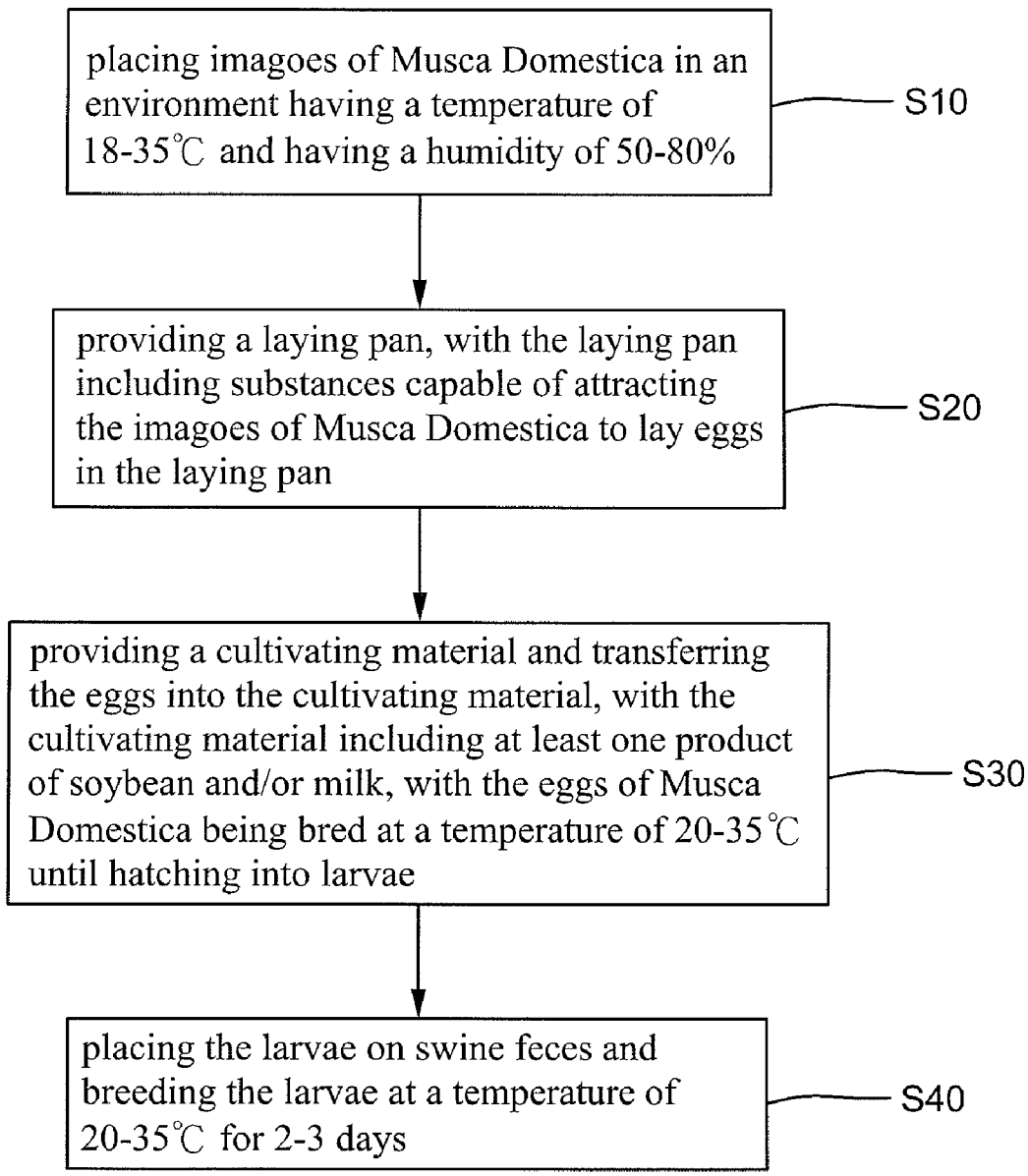

METHOD FOR BREEDING *MUSCA DOMESTICA*

BACKGROUND OF THE INVENTION

The present invention relates to a method for breeding *Musca Domestica* and, more particularly, to a method for increasing the yield and growing speed of larvae of *Musca Domestica*.

*Musca Domestica* (house fly) belongs to family Muscoidea of order Muscomorpha of class Insecta. Characteristics of *Musca Domestica* include wide distribution, short living period, high propagating ability, and high adaptability. *Musca Domestica* is a fully transformed insect that undergoes complete metamorphosis and frequents human habitants. The living stages of *Musca Domestica* include egg, larva, pupa, and imago. Specifically, a larva (maggot) hatches out from an egg and pupates into a pupa in which the tissues and the internals transform. Finally, an imago (*Musca Domestica*) comes out from the pupa in an eclosion stage.

The larvae of *Musca Domestica* have abundant protein, fat, and vitamins and can be dried and added into feedstuff for livestock as an additional nutrient to increase the growing speed of livestock. Furthermore, the larvae of *Musca Domestica* possess active immune substances such as antibacterial substances and interferon that can increase the immunity of living bodies of animals such as human and can be used to cure some diseases. On the other hand, the larvae of *Musca Domestica* feed on feces of livestock and excrete substances that can be used as biofertilizer for plants, avoiding smells and environmental pollution caused by the feces of livestock.

In view of the above advantages, a need exists for a method for breeding *Musca Domestica* to increase the yield of larvae at low costs whole allowing mass-scale breeding of larvae.

BRIEF SUMMARY OF THE INVENTION

To increase the yield and growing speed of the larvae of *Musca Domestica*, the present invention provides a method for breeding *Musca Domestica* including placing imagoes of *Musca Domestica* in an environment having a temperature of 18-35° C. and having a humidity of 50-80%. A laying pan is provided to attract the imagoes of *Musca Domestica* to lay eggs in the laying pan. The laying pan includes substances capable of attracting the imagoes of *Musca Domestica* to lay eggs in the laying pan. The eggs are transferred into a cultivating material including at least one product of soybean and/or milk. The eggs of *Musca Domestica* are bred at a temperature of 20-35° C. until hatching into larvae. The larvae are placed on swine feces and bred at a temperature of 20-35° C. for 2-3 days.

Preferably, the temperature of the environment receiving the imagoes of *Musca Domestica* is 24-26° C.

Preferably, the humidity of the environment receiving the imagoes of *Musca Domestica* is 54-56%.

Preferably, the substances in the laying pan include fermented food.

Preferably, the imagoes of *Musca Domestica* lay eggs in the laying pan after the imagoes of *Musca Domestica* have grown 1-3 days.

Preferably, the eggs of *Musca Domestica* hatch into the larvae in 1-2 days.

Preferably, 2-4 grams of the eggs of *Musca Domestica* are transferred per kilogram of the cultivating material.

Preferably, the cultivating material is received in a Petri dish.

The cultivating material preferably has a water content of 80-95% by weight and more preferably 92% by weight.

Preferably, the cultivating material includes milk powders.

Preferably, the swine feces are received in a Petri dish.

The swine feces preferably have a water content of 80-95% by weight and more preferably 92% by weight.

The method for breeding *Musca Domestica* according to the present invention controls the breeding conditions of the imagoes and larvae of *Musca Domestica* to increase the growing speed of larvae, to shorten the breeding time, to increase the yield of larvae, and to allow subsequent application of using the larvae of *Musca Domestica* as a high protein nutrient.

The present invention will become clearer in light of the following detailed description of illustrative embodiments of this invention described in connection with the drawing.

DESCRIPTION OF THE DRAWING

The drawing shows a block diagram illustrating a method for breeding *Musca Domestica* according to the present invention.

DETAILED DESCRIPTION OF THE INVENTION

With reference to the drawing, a method for breeding *Musca Domestica* according to the present invention includes placing imagoes of *Musca Domestica* in an environment having a temperature of 18-35° C. and having a humidity of 50-80% (S10). A laying pan is provided to attract the imagoes of *Musca Domestica* to lay eggs in the laying pan. Specifically, the laying pan includes substances capable of attracting the imagoes of *Musca Domestica* to lay eggs in the laying pan (S20). The eggs are transferred into a cultivating material including at least one product of soybean and/or milk. The eggs of *Musca Domestica* are bred at a temperature of 20-35° C. until hatching into larvae (S30). The larvae are placed on swine feces and bred at a temperature of 20-35° C. for 2-3 days (S40). Examples of the method for breeding *Musca Domestica* according to the present invention will now be described.

Example 1

Breeding of Imagoes of *Musca Domestica*

An appropriate number of wild *Musca Domestica* were placed in a space and fed with the same food. The wild *Musca Domestica* was tamed after several generations of breeding and propagation, obtaining suitable *Musca Domestica*. The pupae of the tamed *Musca Domestica* before eclosion were placed in an eclosion plate placed in a breeding cage for imagoes. The breeding cage was a sealed net cage having a size of 100-120 cm×60-80 cm×100-200 cm. The imagoes could not fly out of the breeding cage. Furthermore, the breeding cage was placed in a breeding room. The temperature of the breeding room was preferably of 18-35° C., most preferably 24-26° C. The humidity of the breeding room was preferably 50-80%, more preferably 54-56%. Further, the number of imagoes of *Musca Domestica* in the breeding cage was preferably 40,000-120,000. The breeding cage was under the light for 8-16 hours. Since the imagoes do not lay eggs in a dark environment, the breeder can adjust the period of time of the light and the dark according to the time the eggs are to be fetched. Furthermore, a tag can be affixed to the breeding cage to indicate the date on which the imagoes laid eggs and the number of eggs for control purposes.

The pupae of *Musca Domestica* turned into imagoes in 3 or 4 days. After eclosion, a food plate and a water plate were placed into the breeding cage for the imagoes. The foodstuff in the food plate included dairy products (such as milk powders) and sugar that imagoes are fond of. The imagoes began to lay eggs in 1-3 days after eclosion. A laying pan was placed into the breeding cage at that time. A laying pad was received in the laying pan. Substances such as fermented food (fermented milk or the like) capable of attracting the imagoes of *Musca Domestica* were adhered to the laying pad to attract the imagoes to lay eggs on the laying pad. The eggs were gathered periodically, and the laying pad was replaced.

Example 2

Breeding of Larvae of *Musca Domestica*

An appropriate number of eggs of *Musca Domestica* were transferred into a plurality of first Petri dishes. 70-80% of the volume of each first Petri dish was filled with a cultivating material (about 6-8 cm in thickness). The cultivating material included at least one product of soybean and/or milk. A water content of the cultivating material was 80-95% by weight and more preferably 92% by weight. Namely, the solid content of the product of soybean and/or milk of the cultivating material was 5-20% by weight and more preferably 8% by weight. The eggs of *Musca Domestica* were bred at a temperature of 20-35° C. for several days until hatching into larvae (i.e., maggots). The water containing cultivating material provided a moist, nutritive environment for the larvae after hatching. This was the first-stage breeding.

The number of eggs was decided according to the amount of cultivating material received in each first Petri dish. Namely, it was estimated how many larvae could feed on the amount of cultivating material to estimate the number of eggs to be transferred into each first Petri dish. In an example, 2-4 grams of eggs of *Musca Domestica* were transferred per kilogram of cultivating material. The breeding underwent 1-2 days. Each first Petri dish was, but not limited to, a small container having a diameter of 10-12 cm and a height of 8-10 cm.

Swine feces were placed into a plurality of second Petri dishes to a thickness of 4-10 cm. The swine feces (including urine) had a water content of 80-95% by weight and more preferably 92% by weight. An appropriate number of larvae obtained in the first-stage breeding was placed on the swine feces/urine and bred at a temperature of 20-35° C. for 2-3 days. During the breeding period, the larvae fed on the swine feces that provided a moist, nutritive environment for the larvae. This was the second-stage breeding.

The number of larvae was decided according to the amount of swine feces in each second Petri dish. Namely, it was estimated how many larvae could feed on the amount of swine feces to estimate the number of larvae to be transferred into each second Petri dish. Generally, the larvae bred in a first Petri dish were placed into a second Petri dish. Each second Petri dish was, but not limited to, a large container having a length of 60-80 cm, a width of 30-50 cm, and a height of 8-14 cm.

Since the imagoes of *Musca Domestica* are bred indoors in a breeding cage in the method according to the present invention and, thus, isolated from the wild flies that may carry disease-causing bacteria and since the imagoes of *Musca Domestica* feed on clean food including dairy products and sugar, the imagoes can grow in a germless state to reduce the number of the disease-causing bacteria. The larvae are full of high protein and can be used as a nutrient additive for livestock foodstuff or be further processed as edible food for human through procedures meeting the requirements of sanitary regulations for food. On the other hand, the temperature and humidity of each breeding stage (laying eggs, hatching, breeding larvae) of the method according to the present invention are controlled, providing the most suitable environment for growing the *Musca Domestica* (from imagoes to larvae), increasing the yield of eggs, the hatching rate, and the growing speed of larvae.

Furthermore, since two-stage breeding is used from hatching of the eggs through growing of the larvae, the growing speed of the larvae can be increased. Further, the volume of cultivating material received in each first Petri dish (small container) is less than the swine feces received in each second Petri dish (large container), allowing observation of hatching of the eggs and growth of the larvae while assisting in adjustment and control of the first-stage breeding. The hatching rate and growth of the larvae are increased. The problems of low hatching rate and slow growth or even death of larvae resulting from difficulties in control of using large breeding containers are, thus, avoided. The costs of workers and other expenditures for fixing the problems are cut.

In view of the foregoing, the method for breeding *Musca Domestica* according to the present invention increases the yield and application of the larvae of *Musca Domestica* and can be easily carried out. The breeding tools and equipment are simple and inexpensive, allowing mass-scale breeding of *Musca Domestica*.

Although specific embodiments have been illustrated and described, numerous modifications and variations are still possible without departing from the essence of the invention. The scope of the invention is limited by the accompanying claims.

The invention claimed is:

1. A method for breeding *Musca Domestica* comprising:
    placing imagoes of *Musca Domestica* in an environment having a temperature of 18-35° C. and having a humidity of 50-80%;
    providing a laying pan, with the laying pan including substances capable of attracting the imagoes of *Musca Domestica* to lay eggs in the laying pan;
    providing a cultivating material and transferring the eggs into the cultivating material, with the cultivating material including at least one product of soybean or milk, with the eggs of *Musca Domestica* being bred at a temperature of 20-35° C. until hatching into larvae; and
    placing the larvae on swine feces and breeding the larvae at a temperature of 20-35° C. for 2-3 days.

2. The method as claimed in claim 1, with placing the imagoes of *Musca Domestica* in the environment including placing the imagoes of *Musca Domestica* in the environment having a temperature of 24-26° C.

3. The method as claimed in claim 1, with placing the imagoes of *Musca Domestica* in the environment including placing the imagoes of *Musca Domestica* in the environment having a humidity of 54-56%.

4. The method as claimed in claim 1, with providing the laying pan including providing the laying pan including the substances of fermented food.

5. The method as claimed in claim 1, with the imagoes of *Musca Domestica* laying eggs in the laying pan after the imagoes of *Musca Domestica* has grown 1-3 days.

6. The method as claimed in claim 1, with the eggs of *Musca Domestica* hatching into the larvae in 1-2 days.

7. The method as claimed in claim 1, with transferring the eggs including transferring 2-4 grams of the eggs of *Musca Domestica* per kilogram of the cultivating material.

8. The method as claimed in claim 1, with providing the cultivating material including providing the cultivating material in a Petri dish.

9. The method as claimed in claim 1, with providing the cultivating material including providing the cultivating material having a water content of 80-95% by weight.

10. The method as claimed in claim 1, with providing the cultivating material including providing the cultivating material having a water content of 92% by weight.

11. The method as claimed in claim 1, with providing the cultivating material including providing the cultivating material including milk powders.

12. The method as claimed in claim 1, with placing the larvae in the swine feces including placing the larvae in the swine feces received in a Petri dish.

13. The method as claimed in claim 1, with placing the larvae on the swine feces including placing the larvae on the swine feces having a water content of 80-95% by weight.

14. The method as claimed in claim 1, with placing the larvae on the swine feces including placing the larvae on the swine feces having a water content of 92% by weight.

* * * * *